(12) United States Patent
Minton et al.

(10) Patent No.: US 8,501,090 B2
(45) Date of Patent: Aug. 6, 2013

(54) ANTI-MICROBIAL GAS APPARATUS AND METHOD

(76) Inventors: Christian S. Minton, Provo, UT (US); Stephen Minton, Provo, UT (US); John William Randolph Miller, Orem, UT (US)

( * ) Notice: Subject to any disclaimer, the term of this patent is extended or adjusted under 35 U.S.C. 154(b) by 771 days.

(21) Appl. No.: 12/410,442

(22) Filed: Mar. 24, 2009

(65) Prior Publication Data

US 2009/0291022 A1    Nov. 26, 2009

Related U.S. Application Data

(60) Provisional application No. 61/039,064, filed on Mar. 24, 2008.

(51) Int. Cl.
*A61L 9/00* (2006.01)
(52) U.S. Cl.
USPC ............................................................. 422/29
(58) Field of Classification Search
USPC ............................................................. 422/29
See application file for complete search history.

(56) References Cited

U.S. PATENT DOCUMENTS

| | | |
|---|---|---|
| 5,427,797 A | 6/1995 | Frostell et al. |
| 5,713,349 A | 2/1998 | Keaney |
| 5,823,180 A | 10/1998 | Zapol |
| 5,839,433 A | 11/1998 | Higgenbottam |
| 5,873,359 A | 2/1999 | Zapol |
| 6,000,403 A | 12/1999 | Cantwell |
| 6,019,100 A | 2/2000 | Alving et al. |
| 6,063,407 A | 5/2000 | Zapol et al. |
| 6,131,572 A | 10/2000 | Heinonen |
| 6,142,147 A | 11/2000 | Head et al. |
| 6,149,606 A | 11/2000 | Alving et al. |
| 6,432,077 B1 | 8/2002 | Stenzler |
| 6,458,109 B1 | 10/2002 | Henley et al. |
| 6,572,594 B2 | 6/2003 | Satterfield et al. |
| 6,581,599 B1 | 6/2003 | Stenzler |
| 6,601,580 B1 | 8/2003 | Bloch et al. |
| 6,612,306 B1 | 9/2003 | Mault |
| 6,670,323 B1 | 12/2003 | Looker et al. |
| 6,709,681 B2 * | 3/2004 | Benjamin et al. ............. 424/718 |
| 6,786,217 B2 | 9/2004 | Stenzler |
| 6,793,644 B2 | 9/2004 | Stenzler |
| 7,017,573 B1 | 3/2006 | Rasor et al. |
| 7,045,152 B2 | 5/2006 | Stamler |
| 7,122,018 B2 | 10/2006 | Stenzler et al. |
| 2002/0138051 A1* | 9/2002 | Hole et al. .................... 604/305 |
| 2002/0155164 A1* | 10/2002 | Figley et al. .................. 424/600 |
| 2004/0018630 A1* | 1/2004 | Birks et al. .................... 436/116 |
| 2007/0014686 A1* | 1/2007 | Arnold et al. ................... 422/28 |

FOREIGN PATENT DOCUMENTS

| | | |
|---|---|---|
| WO | 2006/110923 | 10/2006 |
| WO | 2007/057763 | 5/2007 |

* cited by examiner

*Primary Examiner* — Michael Marcheschi
*Assistant Examiner* — Christopher Vandeusen
(74) *Attorney, Agent, or Firm* — Pate Baird, PLLC

(57) ABSTRACT

An apparatus and method administering nitric oxide at very high concentrations to healthy skin, tools, implements, support surfaces, and sterile fields to provide sterilization. The apparatus and method providing sterilization in a dry environment lacking the common undesirable effects of anti-microbial soaps and antiseptics.

7 Claims, 4 Drawing Sheets

Overall Data

| Date MM/DD/YY | Gender of Volunteer | Volunteer ID | Cleaning Procedure | Hand | Zone Before Cleaning | Zone After Cleaning |
|---|---|---|---|---|---|---|
| 01/29/08 | Male | 1 | Nitric Oxide | Right | 4 | 2 |
| 01/29/08 | Male | 1 | Soap | Left | 4 | 3 |
| 01/29/08 | Female | 2 | Nitric Oxide | Right | 5 | 2 |
| 01/29/08 | Female | 2 | Soap | Left | 3 | 3 |
| 01/30/08 | Male | 3 | Nitric Oxide | Right | 3 | 1 |
| 01/30/08 | Male | 3 | Soap | Left | 2 | 1 |
| 01/30/08 | Female | 4 | Nitric Oxide | Right | 5 | 3 |
| 01/30/08 | Female | 4 | Soap | Left | 4 | 2 |
| 01/30/08 | Female | 5 | Nitric Oxide | Right | 2 | 0 |
| 01/30/08 | Female | 5 | Soap | Left | 2 | 1 |

FIG. 4

Grading Scale (Zone) Reductions

| Volunteer | Nitric Oxide | Antibacterial Soap |
|---|---|---|
| 1 | 2 Zones | 1 Zone |
| 2 | 3 Zones | 0 Zones |
| 3 | 2 Zones | 1 Zone |
| 4 | 2 Zones | 2 Zones |
| 5 | 2 Zones | 1 Zone |

FIG. 5

Average Grading Scale (Zone) Reductions

| Nitric Oxide | Antibacterial Soap |
|---|---|
| 2.5 Zones | 1 Zone |

FIG. 6

ANTI-MICROBIAL GAS APPARATUS AND METHOD

RELATED APPLICATIONS

This application claims the benefit of U.S. Provisional Patent Application Ser. No. 61/039,064 filed Mar. 24, 2008, which is hereby incorporated by reference.

BACKGROUND

1. The Field of the Invention

This invention relates to anti-microbial materials, processes, and equipment, and more particularly to novel systems and methods for employing nitric oxide gas as a sterilizing agent.

2. The Background Art

Hospitals have a sterilization problem. Documented evidence shows that not everyone washes regularly nor washes effectively. As a result, staph infections still abound.

Nitric oxide (NO) is the subject of Nobel Prize-winning work. The significance of nitric oxide as a vascular relaxing factor is well established. Likewise, it appears that nitric oxide has a topical ability to trigger a reduction of inflammation. For example, nitric oxide has some ability to inhibit those factors responsible for engaging the inflammation response of the body.

Meanwhile, drug-resistant staph infections, antibiotic-resistant strains of bacteria, and the like have become a great concern for the modern medical community. Antibacterial soaps are washed into sewer systems, damaging colonies of useful bacteria as well as fostering resistance in undesirable bacteria. Accordingly, some express a concern that with such ubiquitous use of antibacterial compositions, desirable bacteria will decline in the environment while antibiotic-resistant strains of undesirable bacteria will thrive to displace them in the environment.

Likewise, equipment often requires preparation of liquid sterilization. Chemicals such as alcohol and other antiseptic preparations have environmental effects that may be undesirable, particularly in the long term. Meanwhile, metal instruments can be sterilized by heat in an autoclave. Nevertheless, many instruments now have disposable (i.e., low melting point) plastic handles with metal working surfaces.

An inexpensive process is needed that does not require the heat of an autoclave. What is needed is a material, method, and apparatus for sterilizing or purifying surfaces on instruments as well as skin surfaces of persons. Persons cannot tolerate the temperatures and isolation required for autoclaving instruments. Meanwhile, inexpensive instruments do not tolerate temperature either. What is needed is a manner, material, and system for destroying microbes on the skin of a user, and on surfaces of instruments and other tools used in medical facilities.

BRIEF SUMMARY OF THE INVENTION

In view of the foregoing, in one aspect of an apparatus and method in accordance with the invention, nitric oxide gas may be introduced into an enclosed environment in comparatively extremely high concentrations. Inhaling nitric oxide is a therapy requiring careful monitoring and comparatively low doses to be effective without being toxic. However, healthy skin may be introduced to very high doses over 500 parts per million. Likewise, in one embodiment of an apparatus and method in accordance with the invention, inanimate objects such as surgical tools, other implements, sterile fields, and the like may be exposed to substantially any very high concentration of nitric oxide. The concentration may be applied for sufficient time for the nitric oxide to kill any microbes.

Typically, the transport processes affecting free and forced convection of gases are very much slower than those of liquids. For example, heat transfer, diffusion transport, and the like, whether in free or forced convection, operate more effectively in liquids. For example, scrubbing healthy skin with an anti-microbial liquid will quickly expose the entire surface of the skin to the active ingredient. By contrast, gasses are much less dense, move more slowly, and provide less transport capacity for chemical species, heat, and the like.

Nevertheless, it has been found that creating an enclosed environment to contain nitric oxide, while exposing a material or surface to nitric oxide is very effective. Displacing oxygen, nitric oxide will not support life. Moreover, being somewhat chemically unstable, nitric oxide readily reacts with oxygen. Accordingly, nitric oxide will strip out any oxygen present. Likewise, by being reactive, nitric oxide operates as a chemical radical, scavenging chemicals and thus attacking microbes.

It has been found that an enclosed environment having introduced thereto a flux of nitric oxide, and a flush port for exit thereof can maintain substantially a constant concentration of nitric oxide exposed to the surface all enclosed within the enclosed nitric oxide environment.

It is contemplated that certain embodiments of an apparatus and method in accordance with the invention may rely on concentration gradients to drive diffusion of nitric oxide to contact, engage, and neutralize microbes. Accordingly, it is contemplated that within reason, concentration gradients may be increased in inverse proportion to exposure times. Experiments by applicant have shown substantial reductions in colony counts of bacteria exposed to nitric oxide. According to Fick's law of diffusion, a rate of diffusion is directly proportional to concentration gradients of a material being diffused. Accordingly, the experiments have demonstrated the efficacy of nitric oxide as a sterilizing agent against microbes on healthy skin.

In a direct comparison between scrubbing with antibacterial soaps compared to immersing in a substantially enclosed environment containing exclusively nitric oxide diluted with ambient air, the anti-microbial effects of nitric oxide have been shown to be superior to soaps. Moreover, once released into the atmosphere, nitric oxide may react to more various oxides of nitrogen without long term adverse effects in medically-significant quantities. The invention contemplates that concentrations of from about 500 parts per million up to 1,000,000 parts per million of nitric oxide, substantially pure nitric oxide, may be used to provide sterilization and other microbial effects on healthy skin, surgical instruments, sterile fields, support surfaces, and the like.

Forced convection may be increased in order to increase the exposure concentration and decrease the time required for nitric oxide to contact and sterilize surfaces. According to the transport processes controlled by Fick's law of diffusion, a 15-minute exposure to 1,000 parts per million may be scaled to a 1.5-minute exposure at 10,000 parts per million. Any non-linearaties of scaling may be accommodated by increasing times and increasing the vigor of forced convection flows exposing a surface to nitric oxide.

The invention advances the art in several respects. For example, nitric oxide in accordance with the invention may be applied to healthy tissue, not relying on vascular dilation, and not relying on de-activating the inflammation triggers. Rather, nitric oxide in accordance with the invention may be applied to decontaminate, sterilize, or otherwise destroy microbes directly. Accordingly, very short periods of time may be used at very high concentrations. Exposure times may be as low as five minutes or less. In some embodiments, exposure times of less than one minute may provide substantially complete sterilization of equipment or healthy skin. Exposure times on the order of seconds may rely on nitric oxide moving in forced convection over a surface enclosed in an environment containing a preselected concentration of nitric oxide.

The exposure of healthy tissues or equipment to a single dose of nitric oxide can provide sterilization in accordance with the invention. Meanwhile, the cost of nitric oxide provided by a generator is substantially less expensive on the order of less than one percent of the cost of conventional nitric oxide delivery.

Rather than operating as a drug delivery protocol, a method in accordance with the present invention may operate as a poisoning of microbes. Rather than treating a disease through multiple applications of a drug during multiple weeks of therapy a single dose may provide adequate antisepsis. In one method in accordance with the invention, a single exposure sterilizes a surface, whether a surface of an implement, a supporting surface, a sterile field, or healthy tissues of a subject. A method in accordance with the invention provides an anti-microbial effect in a single exposure sufficiently effective to replace conventional scrubbing with liquid, anti-microbial compositions. By relying on an enclosed environment, concentrations may be controlled. Otherwise, chemical activity as well as uncontrolled dilution may negatively effect the concentration of nitric oxide.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 4 is a table displaying data collected using the experimental method of FIG. 3;

FIG. 5 is a table displaying the reductions in bacterial growth achieved using the experimental method of FIG. 3; and FIG. 6 is a table displaying the average reductions in bacterial growth achieved using the experimental method of FIG. 3.

DETAILED DESCRIPTION OF SELECTED EMBODIMENTS

Figure 1:
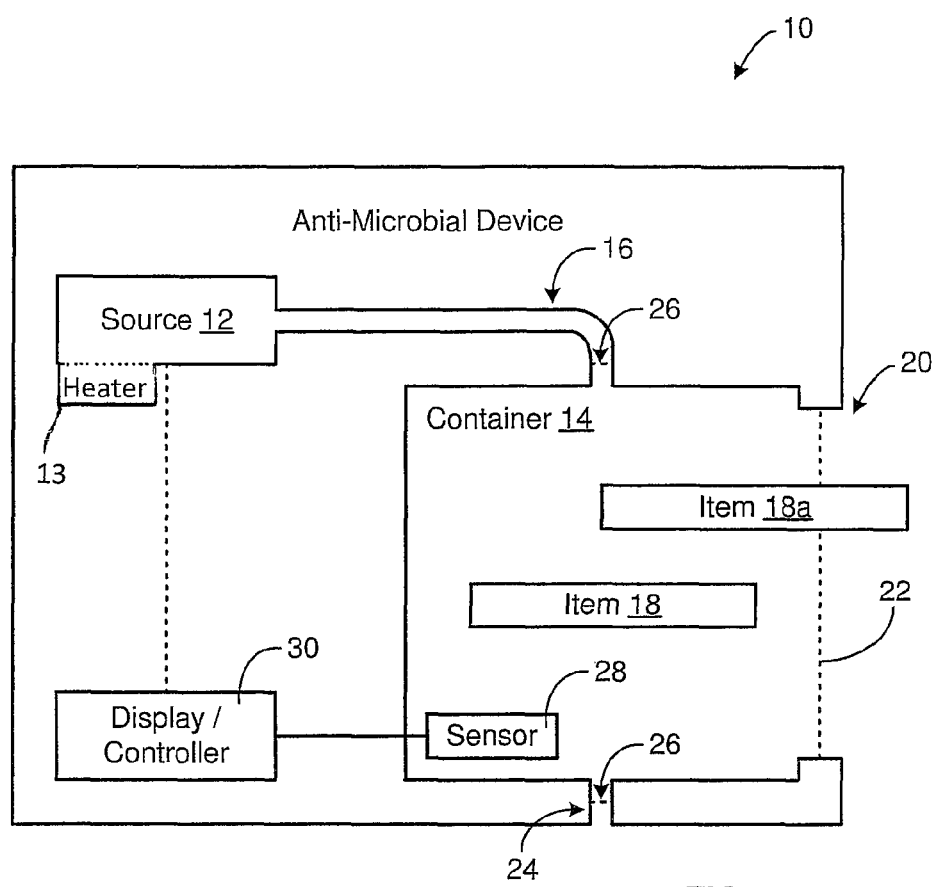
FIG. 1 is a schematic diagram illustrating one embodiment of an anti-microbial device in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings.

Referring to FIG. 1, an apparatus 10 or anti-microbial device 10 in accordance with the present invention may include a source 12 of nitric oxide. A source 12 may be any suitable mechanism for delivering nitric oxide. In selected embodiments, a source 12 may be a tank of nitric oxide. In other embodiments, a source 12 may be a nitric oxide generator. For example, a source 12 may be any of the nitric oxide generators disclosed in U.S. Pat. No. 7,220,393 issued May 22, 2007, U.S. patent application Ser. No. 11/751,523 filed May 21, 2007, U.S. patent application Ser. No. 12/361,123 filed Jan. 28, 2009, U.S. patent application Ser. No. 12/361,151 filed Jan. 28, 2009, U.S. Patent Application Ser. No. 61/025,226 filed Jan. 31, 2008, U.S. Patent Application Ser. No. 61/025,230 filed Jan. 31, 2008, and U.S. Patent Application Ser. No. 61/043,064 filed Apr. 7, 2008, each of which is hereby incorporated by reference.

A source 12 may include a heat source, or heater 13. The heater 13 may be used to heat the contents of the source 12, including without limitation, heating a nitrate and a nitrate in the presence of a metal to produce the desired nitric oxide. The heater 13 may be of any suitable type that can apply heat to the source 12 in a safe, effective manner, including without limitation, heaters that utilize a chemical reaction and may be contained within the apparatus 10, heaters that utilize a fuel that is combusted and may ne contained within the apparatus 10, and heater that utilize electricity and may be contained within the apparatus 10 or may require a connection outside the apparatus 10.

A source 12 may be connected to a container 14 by a conduit 16. The conduit 16 may conduct nitric oxide from the source 12 to the container 14. A container 14 may be any mechanism suitable for maintaining a nitric oxide environment over or around items 18 or surfaces of items 18. A container 14 may be formed of flexible materials, rigid materials, elastic materials or the like. A container 14 may comprise a bag, box, dome or hemisphere, glove, or the like.

Items 18 may be introduced within a container 14 in any suitable manner. Items 18 may be processed through a container 14 in batches. Alternatively, items 18 may pass through a container 14 on a conveyor system. Accordingly, an anti-microbial device 10 in accordance with the present invention may be part of a continuous manufacturing process.

A container 14 in accordance with the present invention may include an opening 20 for introducing items into the container 14 or for exposing the contents of a container 14 to a surface. In selected embodiments, when the apparatus 10 is in use, the opening 20 may be blocked or sealed. For example, a barrier 22 such as a door 22 may close to seal the opening 20. In other embodiments, an item 18a to be sterilized may extend from the interior of the container 14 to the exterior of the container 14. In such embodiments, a barrier 22 may provide a seal between the container 14 and the item 18a.

For example, in certain embodiments, an apparatus 10 in accordance with the present invention may be configured to sterilize the hands of a surgeon. In one such embodiment, the container 14 may be a bag and the barrier 22 may be tape sealing the bag against the arm of the surgeon. In other such embodiments, the container 14 may be substantially rigid e.(g., a box) and the barrier 22 may be an elastic or inflatable structure that seals against the arm or arms of the surgeon.

Thus, a barrier 22 in accordance with the present invention may be adapted according to the intended use of the container 14.

In selected embodiments, a container 14 may include a vent 24 or exhaust port 24. A vent 24 may permit additional nitric oxide to be delivered to the container 14, without increasing the pressure within the container 14. Accordingly, a vent 24 may assist in maintaining a desired concentration of nitric oxide within a container 14.

A vent 24 may include a check valve 26 ensuring that only outgoing flows pass therethrough. If desired or necessary, the conduit 16 may also include a check valve 26. A check valve 26 in the conduit 16 may ensure that only flows from the source 12 to the container 14 may pass through the conduit 14.

An apparatus 10 in accordance with the present invention may include a sensor 28 for monitoring the concentration of nitric oxide within, or delivered to, a container 14. In selected embodiments, a sensor 28 may be connected to a display 30. Accordingly, a user or technician may monitor the concentration of nitric oxide and make adjustments (e.g., to the source 12) as necessary.

Alternatively, a sensor 28 may be connected to a computerized controller 30. Accordingly, a controller 30 may perform certain tasks based on the information received from the sensor 30. For example, a controller 30 may make adjustments as necessary to maintain the desired concentration of nitric oxide within the container 14, controlling the ratio of a stream of nitric oxide to a flow of ambient air. Additionally, a controller 30 may monitor how long the apparatus 10 has been in use and advise a user or technician when a particular sterilization cycle is complete.

Figure 2:
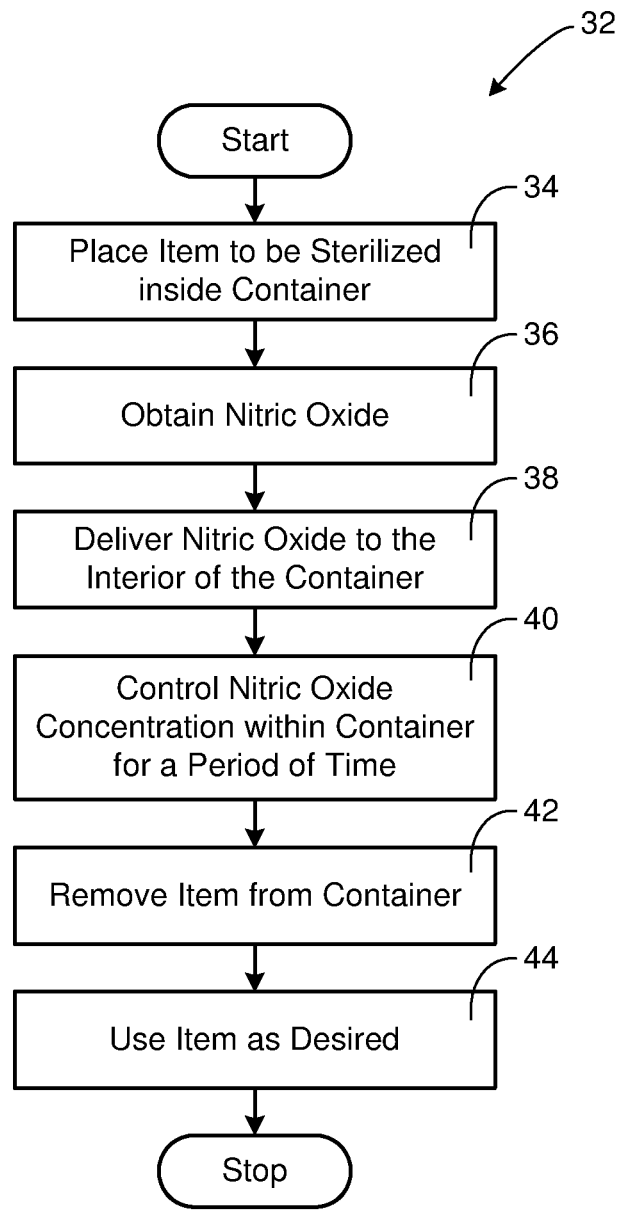
FIG. 2 is a schematic block diagram illustrating one embodiment of an anti-microbial method in accordance with the present invention.

Referring to FIG. 2, a method 32 in accordance with the present invention may begin with placing 34 an item 18 to be sterilized within, or at least in fluid contact with the contents of, the container 14. Once nitric oxide has been obtained 36, it may be introduced 38 into the container 14. The concentration of nitric oxide within the container 14 may be controlled 40 for a period of time. The concentration and time may be selected to ensure that proper sterilization has been achieved. Once the sterilization cycle is complete, the item 18 may be removed 42 from the container 14 and used 44 as desired.

EXAMPLE

Figure 3:
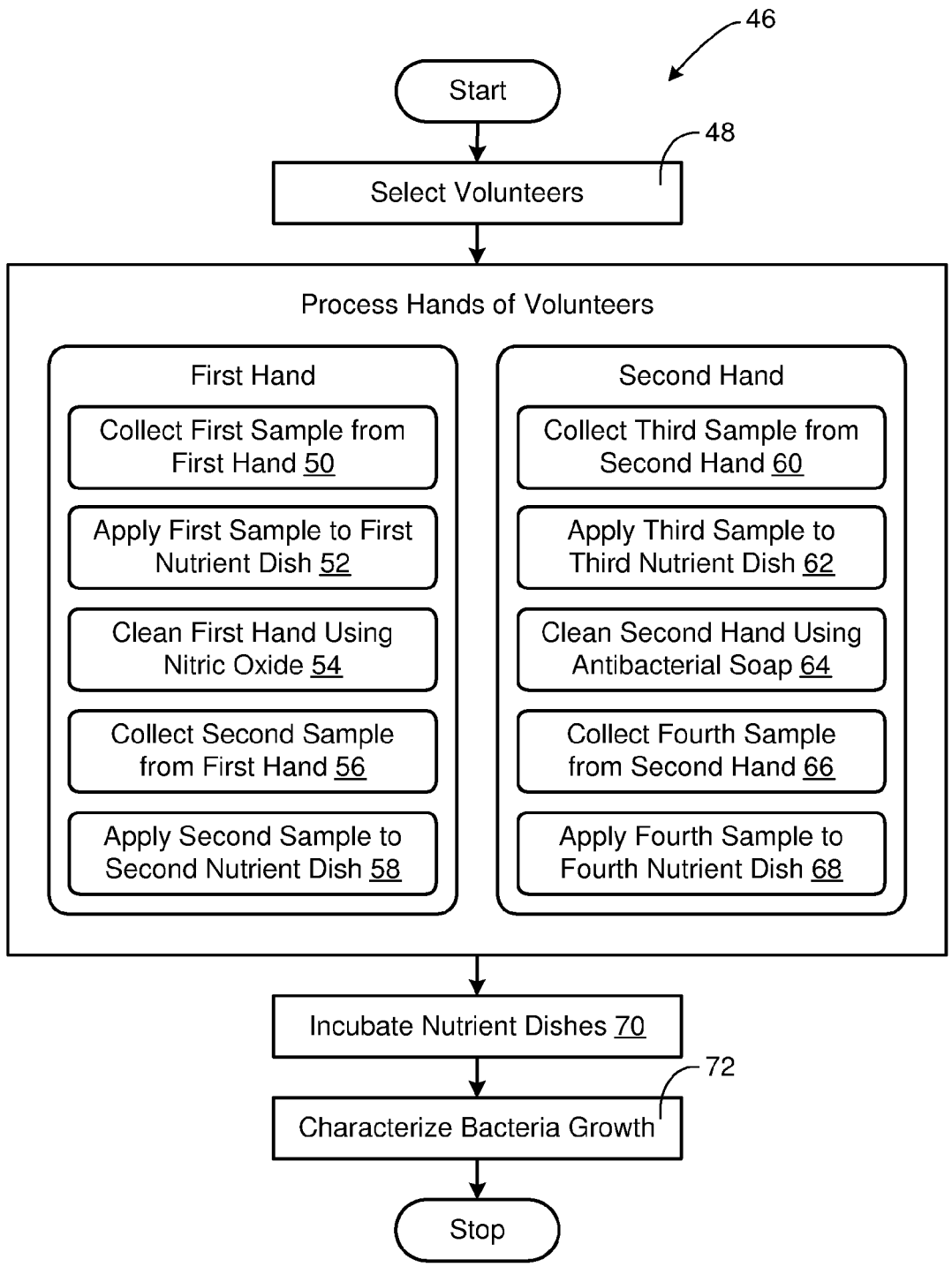
FIG. 3 is a schematic block diagram of one embodiment of an experimental method in accordance with the present invention.

An experiment 46 used to determine the anti-microbial effectiveness of nitric oxide is illustrated in FIG. 3. In the experiment, five volunteers were selected 48. From a first hand of each volunteer, a technician using sterile gloves collected 50 a sample. This was accomplished by rubbing the back of the volunteer's hand with a sterile cotton collection swab for ten seconds. The swab was then applied 52 to a nutrient agar petri dish using the five corner or zone dilution method.

The five corner or zone dilution method involves mechanically diluting bacteria on a streak (blood agar) plate by sequentially spreading the bacteria across the plate in each of five zones. As the concentration of bacteria increases so do the number of zones containing bacteria. Bacteria on agar plate become visible as distinct circular colonies. Each colony represents an individual cell which has divided repeatedly to form a patch. The number of bacteria can be estimated by counting the number of patches or how far the bacteria is diluted by streaking it on the agar plate through the five zones.

After the sample was collected 50, the first hand was cleaned 54 using nitric oxide. This was done by placing the hand of the volunteer into a one-gallon plastic freezer bag. The bag was then inflated with nitric oxide through tubing attached to a portable nitric oxide generator. The open end of the bag was taped closed against the volunteer's forearm. A nitric oxide monitor assisted in keeping the nitric oxide concentration within the bag at 1,000 parts-per-million (ppm).

The volunteer maintained the hand inside the bag for fifteen minutes. After the fifteen minutes, the hand was removed from the bag in a sterile manner (i.e., the hand was not permitted to contact any non-sterile objects). Using sterile gloves and a sterile cotton collection swab, the technician collected 56 a second sample by rubbing the swab on the back of the hand for ten seconds. The swab was then applied 58 to a nutrient dish as explained above.

A similar process was followed with the volunteer's other hand. A technician using sterile gloves collected 60 a sample. This was accomplished by rubbing the back of the volunteer's hand with a sterile cotton collection swab for ten seconds. The swab was then applied 62 to a nutrient agar petri dish using the five corner or zone dilution method.

The second hand was then cleaned 64 using DIAL antibacterial soap. This cleaning lasted two minutes and was accomplished using the volunteers convention hand wasting techniques. After the second hand was cleaned 64, the technician used sterile gloves and a sterile cotton collection swab to collect 66 a sample by rubbing the swab on the back of the hand for ten seconds. The swab was then applied 68 to a nutrient dish as explained above.

The nutrient dishes were then incubated at thirty-five degrees Celsius for forty-eight hours. Using a zone-based grading scale for bacterial colonization, the technician then graded 72 the dishes for each volunteer. On this scale, bacteria growth extending no further than zone 1 was characterized as "zone 1," bacteria growth extending no further than zone 2 was characterized "zone 2," etc. Accordingly, the higher the zone number, the greater the number of bacteria.

The data collected from the experiment is present in FIGS. 4-6. From the data, it can be seen that hands exposed to 1,000 ppm of nitric oxide for fifteen minutes had a lower bacterial colony count than hands washed with DIAL antibacterial soap for 2 minutes.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method comprising:
   providing a surface to be sterilized;
   substantially enclosing the surface within a volume;
   providing a container defining the volume and comprising an inlet and an exit;
   providing a generator generating a stream of nitric oxide, wherein the generator delivers the stream at negative gage pressure;
   providing a conduit connecting the generator to the inlet;
   controlling incursion of air into the volume from an external environment thereof;
   introducing into the volume a preselected concentration of nitric oxide, wherein introducing comprises conducting the stream from the generator through the conduit to the inlet;
   providing a controller maintaining the preselected concentration of nitric oxide;

waiting a preselected time for the nitric oxide to sterilize the surface;

removing the surface from the volume; and using the surface in an application requiring the surface to be sterile.

2. A method comprising:

providing a surface to be sterilized;

substantially enclosing the surface within a volume;

controlling incursion of air into the volume from an external environment thereof;

introducing into the volume a preselected concentration of nitric oxide, and generating the nitric oxide at negative gage pressure;

waiting a preselected time for the nitric oxide to sterilize the surface;

removing the surface from the volume; and using the surface in an application requiring the surface to be sterile.

3. The method of claim 2, wherein generating further comprises heating a nitrite and a nitrate in the presence of a metal.

4. A method comprising:

obtaining a container providing a controlled environment, defining a volume limiting incursion of ambient air thereinto, and comprising an inlet and an exit;

obtaining a generator generating a stream of nitric oxide, wherein the stream is substantially pure nitric oxide;

operating the generator to deliver the stream at negative gage pressure;

arranging a conduit conducting the stream from the generator to the inlet;

selecting a surface to be sterilized;

substantially enclosing the surface within the volume;

controlling incursion of air into the volume from an external environment thereof;

connecting the generator to the inlet of the container;

introducing into the volume a preselected concentration of nitric oxide;

providing a controller maintaining the preselected concentration of nitric oxide;

waiting a preselected time for the nitric oxide to sterilize the surface; and removing the surface from the volume.

5. The method of claim 4, wherein the generator further comprises a heater providing energy into a nitrite and a nitrate in the presence of a metal.

6. The method of claim 5, further comprising controlling by the controller, a concentration of the nitric oxide to a preselected concentration value for the preselected time, rendering the surface sterilized of microbes to a preselected sterilization value corresponding to a sterilization criterion.

7. The method of claim 6 wherein the surface is at least one of:

the skin of a hand of a user; or a tool used by the user.

* * * * *